United States Patent [19]

Odorisio et al.

[11] Patent Number: 5,019,612
[45] Date of Patent: May 28, 1991

[54] 6-(4-HYDROXYPHENYL)-4,5-DIHYDRO-3(2H)-PYRIDAZINONES AND STABILIZED COMPOSITIONS

[75] Inventors: Paul A. Odorisio, Edgewater, N.J.; Stephen D. Pastor, Yonkers, N.Y.

[73] Assignee: Ciba-Geigy Corporation, Ardsley, N.Y.

[21] Appl. No.: 391,214

[22] Filed: Aug. 8, 1989

Related U.S. Application Data

[62] Division of Ser. No. 915,446, Oct. 6, 1986, Pat. No. 4,888,423.

[51] Int. Cl.$^5$ .............................................. C08K 5/3477
[52] U.S. Cl. ........................................ 524/99; 524/100
[58] Field of Search .................. 252/403; 524/99, 100; 544/238, 239; 560/53

[56] References Cited

U.S. PATENT DOCUMENTS

| | | | |
|---|---|---|---|
| 3,377,154 | 4/1968 | Reichemeder et al. | 71/92 |
| 4,011,321 | 3/1977 | Coates et al. | 514/247 |
| 4,397,854 | 8/1983 | Sircar | 514/247 |
| 4,888,423 | 12/1989 | Odorisio et al. | 544/238 |

FOREIGN PATENT DOCUMENTS 178189  4/1986  European Pat. Off. ............ 544/239

Primary Examiner—Kriellion Morgan
Attorney, Agent, or Firm—Luther A. R. Hall

[57] ABSTRACT 6-(4-hydroxyphenyl)-4,5-dihydro-3(2H)-pyridazinones of formula I

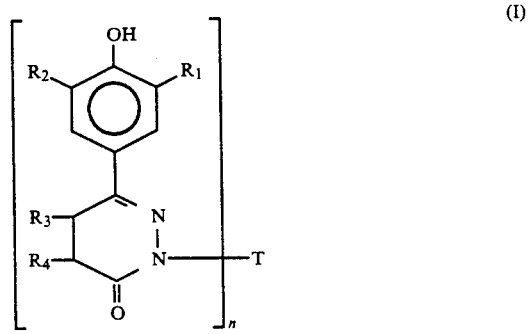

where $R_1$ and $R_2$ are independently alkyl, cycloalkyl, aryl or aralkyl, $R_3$ and $R_4$ are independently hydrogen or alkyl, n is 1 to 4 and T is hydrogen, alkyl, substituted alkyl, alkylene or arylene, are effective in stabilizing organic materials against oxidative, thermal and actinic degradation.

10 Claims, No Drawings

6-(4-HYDROXYPHENYL)-4,5-DIHYDRO-3(2H)-PYRIDAZINONES AND STABILIZED COMPOSITIONS

This is a divisional of application Ser. No. 915,446 filed on Oct. 6,1986 now U.S. Pat. NO. 4,888,423 issued on Dec. 19 1989.

The present invention relates to novel 6-(4-hydroxyphenyl)-4,5-dihydro-3(2H)-pyridazinones and their use as stabilizers in various organic materials.

BACKGROUND OF THE INVENTION

A number of pyridazinone (sometimes called pyridazone) compounds are known.

U.S. Pat. No. 3,377,154 describes ester substituted derivatives of 5-amino-4-halo-2-phenyl-3(2H)-pyridazinones as herbicides.

German Patent No. 1,670,295 teaches the use of 4,4,5,5-tetra-halo-3(2H)-pyridazinones as flame retardants.

U.S. Pat. No. 4,011,321 describes 6-(3-substituted amino-2-hydroxypropoxyphenyl)-4,5-dihydro-3(2H)-pyridazinones as β-adrenergic blocking agents.

U.S. Pat. No. 4,397,854 pertains to selected 6-phenyl-4,5-dihydro-3(2H)-pyridazinones which are useful in pharmaceutical compositions as cardiotonic agents. While the pyridazinones of this patent may be selectively substituted on the 6-phenyl group, the instant compounds having a hindered phenolic moiety at the 6-position of the 3(2H)-pyridazinone are not disclosed or suggested. This patent is totally silent as to whether the cardiotonic agents set forth therein, each having a pyridazinone moiety in the molecule, have any stabilization properties as well.

OBJECTS OF THE INVENTION

One object of the instant invention is to provide new substituted 6-(4-hydroxyphenyl)-4,5-dihydro-3(2H)pyridazinones which have stabilization properties for organic materials subject to oxidative, thermal and/or actinic degradation.

A further object is to provide stabilized compositions containing the pyridazinone compounds of this invention.

DETAILED DISCLOSURE

The instant invention pertains to substituted 6-(4-hydroxyphenyl)-4,5-dihydro-3(2H)-pyridazinone compounds of formula I

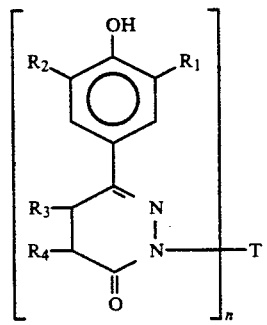

(I)

wherein $R_1$ is alkyl of 3 to 8 carbon atoms, cycloalkyl of 5 to 8 carbon atoms, phenyl, said phenyl substituted by alkyl of 1 to 18 carbon atoms, aralkyl of 7 to 9 carbon, or said aralkyl substituted by alkyl of 1 to 4 carbon atoms, $R_2$ is alkyl of 1 to 18 carbon atoms, cycloalkyl of 5 to 8 carbon atoms, phenyl, said phenyl substituted by alkyl of 1 to 18 carbon atoms, aralkyl of 7 to 9 carbon atoms or said aralkyl substituted by alkyl of 1 to 4 carbon atoms, $R_3$ and $R_4$ are independently hydrogen or alkyl of 1 to 4 carbon atoms, n is an integer of 1 to 4, and when n is 1, T has the meaning of $R_2$ or T is hydrogen or alkyl of 1 to 5 carbon atoms substituted by hydroxyl, by halogen, by alkoxy of 1 to 12 carbon atoms, by thioalkyl of 1 to 18 carbon atoms, by carboalkoxy of 2 to 19 carbon atoms or by -OCOG where G is alkyl of 1 to 18 carbon atoms, phenyl, phenyl substituted by alkyl of 1 to 4 carbon atoms, or T is 2-pyridyl, 3-pyridyl or 4-pyridyl, or when n is 2 to 4, T is the group

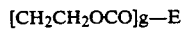

where, when n and g are 2, E is a direct bond or a straight or branched chain alkylene of 2 to 10 carbon atoms, cyclohexylene or arylene of 6 to 10 carbon atoms, when n and g are 3, E is propane-1,2,3-triyl, benzene-1,3,5-triyl or benzene-1,2,4-triyl, or when n and g are 4, E is butane-1,2,3,4-tetrayl, benzene-1,2,4,5-tetrayl or benzophenone-3,3',4,4'-tetrayl.

The preferred embodiments of the compounds of formula I are those where $R_1$ is alkyl of 4 to 8 carbon atoms, most preferably tetra-butyl; where $R_2$ is alkyl of 1 to 8 carbon atoms, most preferably tetra-butyl; where $R_3$ and $R_4$ are each hydrogen; where n is 1 or 2; and where, when n is 1, T is hydrogen, alkyl of 1 to 8 carbon atoms, phenyl, alkyl of 1 to 5 carbon atoms substituted by hydroxyl, by halogen or by —OCOG where G is alkyl of 1 to 18 carbon atoms; or when n is 2, T is the group

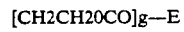

where g is 2 and E is alkylene of 2 to 10 carbon atoms.

Most preferably when n is 1, T is hydrogen, phenyl, 2-hydroxyethyl or 2-bromoethyl.

Most preferably when n is 2, T is the group [CH2CH2OCO]g—E where g is 2 and E is alkylene of 4 to 8 carbon atoms.

When $R_1$, $R_2$, $R_3$, $R_4$, T or G are alkyl, the alkyl depending on the carbon atom range recited for each group, include for example methyl, ethyl, isopropyl, n-butyl, sec-butyl, tert-butyl, tert-amyl, n-hexyl, 2-ethylhexyl, isooctyl, n-octyl, nonyl, decyl, n-dodecyl, tridecyl, tetradecyl, hexadecyl and n-octadecyl and branched isomers thereof.

Cycloalkyl of 5 to 8 carbon atoms includes for example cyclopentyl, cyclohexyl, cycloheptyl and cyclooctyl.

When $R_1$, $R_2$ or T is phenyl or aralkyl substituted by alkyl of 1 to 18 carbon atoms, examples of such alkyl groups are given above. Examples of such substituted phenyl groups are tolyl, xylyl, mesityl and ethylphenyl.

When $R_1$, $R_2$ or T is aralkyl of 7 to 9 carbon atoms, examples of such groups are benzyl, phenethyl, alpha-methylbenzyl and alpha, alpha-dimethylbenzyl (=alpha-cumyl).

When T is substituted alkyl of 1 to 5 carbon atoms, examples of such groups are methyl, ethyl, propyl, butyl or amyl which are substituted by hydroxyl; by halogen such as chlorine, fluorine or bromine; by alkoxy such as methoxy, ethoxy, butoxy, octyloxy, decyloxy or dodecyloxy; by carboalkoxy of 2 to 19 carbon atoms where the group is —COO-alkyl of 1 to 18 carbon atoms; or by —OCOG where G is defined above.

Preferably T can be, for example, 2-hydroxyethyl, 2-chloroethyl, 2-bromoethyl, 3-hydroxypropyl or 2-hydroxypropyl.

When E is alkylene of 2 to 10 carbon atoms, E can be e.g. straight-chain or branched $C_2$-$C_{10}$-alkylene such as, for example, ethylene, trimethylene, tetramethylene, pentamethylene, 2,2-dimethylpropane-1,3-diyl, hexamethylene, heptamethylene, octamethylene, decamethylene, 2,2-pentamethylenepropane-1,3-diyl.

When E is for example arylene of 6 to 10 carbon atoms, E is phenylene, phenylene substituted by one or more $C_1$-$C_4$-alkyl or naphthylene.

The instant invention also pertains to a stabilized composition which comprises (a) an organic material subject to oxidative, thermal or actinic degradation, and (b) an effective stabilizing amount of a compound of formula I.

The compositions where component (a) is a synthetic polymer are especially part of this invention, and most particularly when the synthetic polymer is a polyolefin such as polypropylene.

The instantly claimed compounds are effective stabilizers for organic materials or compositions of matter comprising organic materials in that they reduce degradation resulting from long term oxidative and/or thermal ageing and effectively protect said materials from actinic radiation.

In addition, the inventive compounds show little tendency to evaporate from the organic materials during thermal processing. Thus, the loss of these compounds during such processing is negligible.

The starting materials for making the instant compounds of formula I are largely items of commerce for example the hindered phenols such as 2,6-di-tertbutylphenol; the monosuccinyl chlorides such as β-carbomethoxypropionyl chloride; the hydrazines such as hydrazine, phenylhydrazine and 2-hydroxyethylhydrazine.

The instant compounds of formula I are preferably prepared by first reacting a hindered phenol with a mono ester monosuccinyl chloride using a Friedel-Crafts catalyst to give the corresponding intermediate ester

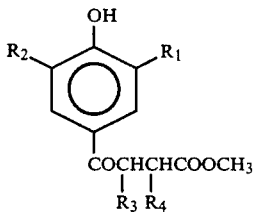

This ester is then reacted with hydrazine or substituted hydrazine (NH2NHT) to give the compounds of formula I.

When in the compound of formula I, T is H or alkyl substituted by OH, additional derivatives also falling within the scope of formula I are prepared by reacting said compound with aldehydes, mercaptans, alcohols, acid chlorides or acrylate esters.

The synthesis of the compounds of the formula I is illustrated in detail in the Examples listed below.

Depending on the nature of the polymer or organic material and the specific end-use application, the compounds of the formula I are employed in amounts of from about 0.01 to about 5% by weight of the stabilized composition. An advantageous range is from 0.5 to 2%, and in particular from 0.1 to 1%.

In general, polymers and organic materials which can be stabilized by the instant compounds include 1. Polymers of monoolefins and diolefins, for example polyethylene (which optionally can be crosslinked), polypropylene, polyisobutylene, polybutene-1, polymethyl-pentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA or AES—polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example, 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example, 2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example 2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,

2'-methylene-bis-(6-tert.butyl-4-methylphenol)
2,2'-methylene-bis-(6-tert.butyl-4-ethylphenol)
2,2'-methylene-bis-[4-methyl-6-($\alpha$-methylcyclohexyl)-phenol]
2,2'-methylene-bis-(4-methyl-6-cyclohexylphenol)

2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-ndodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.-butyl-4-methylphenyl]-terephthalate.

1.5. Benzyl compounds, for example, 1,3,5-tri-(3,5-di-tert.butyl-4-hydroxybenzyl)-2,4,6-trimethylbenzene-di-(3,5-di-tert.butyl-4-hydroxybenzyl)sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl-)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example, 4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of
β-(3,5-di-tert-butyl-4-hydroxyphenyl)propionic acid with monohydric or polyhydric alcohols, for example,

| methanol | diethyleneglycol |
|---|---|
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Esters of
β-(5-tert-butyl-4-hydroxy-3-methylphenyl)propionic acid with monohydric or polyhydric alcohols, for example,

| methanol | diethyleneglycol |
|---|---|
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of
β-(3,5-di-tert-butyl-4-hydroxyphenyl)propionic acid for example,

N,N'-di-(3,5-di-tert.butyl-4-hydroxyphenylpropionyl)-hexamethylenediamine
N,N'-di-(3,5-di-tert.butyl-4-hydroxyphenylpropionyl)-trimethylenediamine
N,N'-di-(3,5-di-tert.butyl-4-hydroxyphenylpropionyl)-hydrazine 2. UV absorbers and light stabilisers
2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert. butyl-, 5-chloro-3'-tert.butyl-5'-methyl-, 3'-sec.butyl5'-tert.butyl-, 4'-octoxy, 3',5'-di-tert.amyl-, 3',5'-bis-(α, α-dimethylbenzyl)-derivative.
2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivative.
2.3. Esters of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butyl-phenyl ester and 3,5-di-tert.-butyl-4-hydroxybenzoic acid hexadecyl ester.
2.4. Acrylates, for example, β-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.
2.5 Nickel compounds, for example, nickel complexes of
2,2'-thio-bis-[4-(1,1,3,3-tetramethylbutyl)-phenol], such as the 1:1 or 1:2 complex, optionally with additional ligands such as n-butylamine, triethanolamine or N-cyclo-hexyl-di-ethanolamine, nickel dibutyldithiocarbamate, nickel salts of 4-hydroxy-3,5-di-tert.butyl-benzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.
2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).
2.7. Oxalic acid diamides, for example, 4,4'-dioctyloxyoxanilide, 2,2'-di-octyloxy-5,5'-di-tert.butyloxanilide, 2,2'-di-dodecyloxy-5,5'-di-tert.butyl-oxanilide, 2-ethoxy2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o-and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-.butyl4-hydroxyphenylpropionyl)-hydrazine, 3-salicyloylamino1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbite triphosphite, tetrakis-(2,4-di-tert.butylphenyl)-4,4'diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

5a. Hydroxylamines, for example, N,N-dibenzylhydroxylamine, N,N-di-n-octylhydroxylamine, N,N-diethylhydroxylamine, N,N-dicyclohexylhydroxylamine.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

Without further elaboration, one skilled in the art can, using the preceding description, utilize the present invention to its fullest extent. The following preferred specific embodiments are, therefore, to be construed as merely illustrative and not limitative to the remainder of the disclosure in any way whatsoever.

EXAMPLE 1

6-(3,5-Di-tert-butyl-4-hydroxyphenyl)-4,5-dihydro-3(2H)pyridazinone

A mixture of 22 g (0.07 mol) methyl 4-(3,5-di-tert-butyl-4-hydroxyphenyl)-4-oxo-butanoate and 6.8 g (0.18 mol) of 85% aqueous hydrazine in 250 ml of ethanol is heated under reflux. The reaction is considered complete by the disappearance of the starting material as indicated by TLC analysis (silica gel; 7/3: hexane/ethyl acetate). Upon cooling the reaction mixture, 18.0 g (85% yield) of white crystals are collected by filtration: mp 200–203° C; IR ($CH_2Cl_2$) 3640, 3420, 3250 and 1680 cm$^{-1}$.

Anal. Calcd. for $C_{18}H_{26}N_{22}$: C, 71.5; H, 8.7; N, 9.3.
Found: C, 71.4; H, 8.6; H, 9.4.

EXAMPLE 2

6-(3,5-Di-tert-butyl-4-hydroxyphenyl)-4,5-dihydro-2-phenyl3(2H)-pyridazinone

The procedure of Example 1 is followed using 15 g (0.047 mol) of methyl 4-(3,5-di-tert-butyl-4-hydroxyphenyl)-4-oxo-butanoate; 7.3 g (0.067 mol) of phenylhydrazine and 250 ml of ethanol.

The reaction residue is purified by chromatography (silica gel; dichloromethane and ethyl acetate eluent) followed by recrystallization from dichloromethane/hexane to give 7.2 g (40% yield) of white crystals: mp 167–170° C; IR ($CH_2Cl_2$) 3625 and 1680 cm$^{-1}$.

Anal. Calcd. for C24H30N202 C, 76.2; H, 8.0; N, 7.4.
Found: C, 75.9; H, 8.3; N, 7.4.

EXAMPLE 3

6-(3,5-Di-tert-butyl-4-hydroxyphenyl)-4,5-dihydro-2-(2-hydroxyethyl)-3(2H)-pyridazinone The procedure of Example 1 is followed using 32.0 g (0.1 mol) of methyl 4-(3,5-di-tert-butyl-4-hydroxyphenyl)4-oxo-butanoate, 7.6 g (0.1 mol) of 2-hydroxyethylhydrazine and 150 ml of n-butanol.

Upon cooling, 23 g (66% yield) of white solid are collected by filtration: mp 140–143° C; IR ($CH_2Cl_2$) 3620, 3450 (br), 1680 cm$^{-1}$.

Anal. Calcd. for $C_{20}H_{30}N_2O_3$: C, 69.3; H, 8.7; N, 8.1.
Found: C, 69.0; H, 8.9; N, 7.8.

EXAMPLE 4

Bis-2,2'-[6-(3,5-di-tert-butyl-4-hydroxyphenyl)-4,5-dihydro-3(2H)-pyridazin-2-yl]ethyl sebacate To a cooled suspension of 6.93 g (0.02 mol) of the product of Example 3 and 2.02 g (0.02 mol) of triethylamine in 250 ml of ether at 5° C is added dropwise 2.30 g (0.01 mol) of sebacoyl chloride. After the addition is complete, the reaction mixture is heated at 30–35° C until the disappearance of the acid chloride carbonyl absorption in the IR spectrum of a reaction aliquot (approximately 3-4 hours) is observed. Upon cooling, the triethylamine hydrochloride salt is removed by filtration and the product isolated by concentration of the filtrate in vacuo.

The reaction residue is purified by chromatography (silica gel; dichloromethane and ethyl acetate eluent) to give 5.2 g (60% yield) of off-white solid: mp 112–116° C; IR ($CH_2Cl_2$) 3620, 1735, and 1680 cm$^{-1}$.

Anal. Calcd. for $C_{50}H_{74}N_4O_8$: C, 69.9; H, 8.7; N, 6.5.
Found: C, 70.2; H, 9.1; N, 6.5.

EXAMPLE 5

Bis-2,2'-[6-(3,5-di-tert-butyl-4-hydroxyphenyl)-4,5-dihydro-3(2H)-pyridazin-2-yl]ethyl adipate The procedure of Example 4 is followed using 28.3 g (0.082 mol) of the product of Example 3, 8.3 g (0.082 mol) of triethylamine, 7.5 g (0.041 mol) of adipoyl chloride and 500 ml of ether.

The reaction residue is purified by chromatography (silica gel; dichloromethane and ethyl acetate eluent) to give 8.3 g of a yellow glass which is recrystallized from a mixture of dichloromethane and hexane to give 5.1 g (16%) of white crystals: mp 105–108° C; IR (CH$_2$Cl$_2$) 3620, 1735 and 1680 cm$^{-1}$.

Anal. Calcd. for C$_{46}$H$_{66}$N$_4$O$_8$: C, 68.8; H, 8.3; N, 7.0. Found: C, 68.3; H, 8.3; N, 6.3.

EXAMPLE 6

2-(2-Bromoethyl)-6-(3,5-di-tert-butyl-4-hydroxyphenyl)4,5-dihydro-3(2H)-pyridazinone To a suspension of 3.47 g (0.01 mol) of the product of Example 3 in 20 ml of glacial acetic acid is added dropwise a solution of 1.6 g (0.01 mol) of bromine in 5 ml of glacial acetic acid. After the addition is complete, the reaction mixture is heated at 60° C. The progress of the reaction is followed by TLC analysis (silica gel; 5% methyl alcohol in dichloromethane) of a reaction aliquot. The reaction is considered complete by the disappearance of the starting material as indicated by TLC analysis. The cooled reaction mixture is diluted with water and extracted with ether. The ether layer is washed sequentially with water, aqueous sodium metabisulfite, aqueous sodium bicarbonate and brine. After drying over anhydrous sodium sulfate and concentrating in vacuo, the reaction residue is treated with methanol to give 1.2 g (29% yield) of white solid: mp 141–144° C; IR (CH$_2$Cl$_2$) 3625 and 1675 (br) cm$^{-1}$.

Anal. Calcd. for C20H29BrN202 C, 58.7; H, 7.1; N, 6.8. Found: C, 58.7; H, 7.1; N, 6.8.

EXAMPLE 7

The oxidation stability of milled polypropylene samples, containing the indicated stabilizers, is measured on plaques of 25 mil (0.635 mm) thickness on exposure to air in a forced draft oven at 150° C. The plaques are considered to have failed on showing the first signs of decomposition (e.g., cracking or brown edges).

| Additive Compound of | Additive Concentration | Oxidative Stability Time to Failure (Hours) |
|---|---|---|
| Base Resin | — | <20 |
| Base Resin with 0.3% DSTDP | — | <20 |
| Example 4 | 0.2% | 100 |
| Example 4 with 0.3% DSTDP | 0.1% | 970 |

DSTDP—Distearyl thiodipropionate

EXAMPLE 8

The oxidation stability of milled polypropylene samples, containing the indicated stabilizers, is measured in stretched tapes of 2 mil (0.05 mm) thickness on exposure to air in a forced draft oven at 115° C. The tapes are considered to have failed on showing the first signs of decomposition (e.g., embrittlement).

| Additive Compound of | Additive Concentration | Oxidative Stability Time to Failure (Hours) |
|---|---|---|
| Base Resin | None | 96–165 |
| Example 4 | 0.2 | 660 |

EXAMPLE 9

This Example illustrates the light stabilizing effectiveness of the instant stabilizers in rigid polyvinyl chloride.

The following rigid polyvinyl chloride formulation is utilized in this example.

| Formulation | Parts |
|---|---|
| Polyvinyl Chloride Resin[1] | 100 |
| Methacrylic acid/ester processing aid | 2.0 |
| Acrylic impact modifier | 7.0 |
| Calcium Stearate | 0.8 |
| Paraffin wax | 0.2 |
| Polyethylene wax | 1.0 |
| Tin mercaptide[2] | 2.0 |
| Titanium dioxide (rutile, non-chalking) | 5.0 |
| Light stabilizer | 1.0 |

[1]GEON 103 EP-F76 from B F Goodrich Co.
[2]Thermolite T-137 from M & T Chemicals.

The ingredients are blended including the indicated amounts of titanium dioxide and stabilizer. The samples are milled on a two roll mill (front roll @ 171° C - back roll @ 165° C) for a period of three minutes after band formation. The resulting material is then compression molded (temperature 182° C, 2 minutes no pressure; 1 minute pumping pressure; 2 minutes full pressure then cool to 38° C) into test plaques (5.1 cm×5.1 cm). The formulated samples are exposed in Xenon Weatherometer at black panel temperature of 55°–60° C and relative humidity of 70–75%. Samples are withdrawn at periodic intervals and yellowness index measured according to ASTM D-1925-63T. Higher values are indicative of lower stability.

| Light Stabilizer | Conc. Stab. (phr) | Conc. TiO (phr) | Yellowness Index 1532 Hrs | 2030 Hrs | 3035 Hrs |
|---|---|---|---|---|---|
| none | — | 5.0 | 24.4 | 27.4 | 30.4 |
| of Example 1 | 1.0 | 5.0 | 20.5 | 24.1 | 29.9 |

EXAMPLE 10

This Example illustrates the light stabilizing effectiveness of the instant stabilizers in polypropylene.

Unstabilized polypropylene powder (Hercules Profax 6501) is thoroughly blended with the indicated amount of additive. The blended materials are then milled on two-roll mill at 182° C for five minutes, after which time the stabilized polypropylene is sheeted from the mill and allowed to cool. The milled polypropylene is then cut into pieces and compression molded on a hydraulic press at 220° C and 175 psi (1.2×106 Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by Weight) | FS/BL Test Results (Hours to Failure) |
|---|---|---|
| Base Resin | — | 190–200 |
| Example 1 | 0.2 | 290 |
| Example 2 | 0.2 | 290 |

| Additive Compound of | Additive Concentration (% by Weight) | FS/BL Test Results (Hours to Failure) |
|---|---|---|
| Example 3 | 0.2 | 290 |

What is claimed is:

1. A stabilized composition which comprises
   (a) A synthetic polymer subject to oxidative, thermal or actinic degradation, and
   (b) an effective stabilizing amouunt of a compound of formula Ia or Ib (Ia)    (Ib)

wherein
   $R_1$ is alkyl of 3 to 8 carbon atoms, cycloalkyl of 5 to 8 carbon atoms, phenyl, said phenyl substituted by alkyl of 1 to 18 carbon atoms, aralkyl of 7 to 9 carbon, or said aralkyl substituted by alkyl of 1 to 4 carbon atoms,
   $R_2$ is alkyl of 1 to 18 carbon atoms, cycloalkyl of 5 to 8 carbon atoms, phenyl, said phenyl substituted by alkyl of 1 to 18 carbon atoms, aralkyl of 7 to 9 carbon atoms or said aralkyl substituted by alkyl of 1 to 4 carbon atoms,
   $R_3$ and $R_4$ are independently hydrogen or alkyl of 1 to 4 carbon atoms,
   g is an integer of 2 to 4,
   T has the meaning of $R_2$ or T is hydrogen or alkyl of 1 to 5 carbon atoms substituted by hydroxyl, by halogen, by alkoxy of 1 to 12 carbon atoms, by thioalkyl of 1 to 18 carbon atoms, by carboalkoxy of 2 to 19 carbon atoms or by -OCOG where G is alkyl of 1 to 18 carbon atoms, phenyl, phenyl substitued by alkyl of 1 to 4 carbon atoms, or T is 2-pyridyl, 3-pyridyl or 4-pyridyl, and
   when g is 2, E is a direct bond or straight or branched chain alkylene of 2 to 10 carbon atoms, cyclohexylene or arylene of 6 to 10 carbon atoms,
   when g is 3, E is propane-1,2,3-triyl, benzene-1,3,5-triyl or benzene-1,2,4-triyl, or
   when g is 4, E is butane-1,2,3,4-tetrayl, benzene-1,2,4,5-tetrayl or benzophenone-3,3'4,4'-tetrayl.

2. A composition according to claim 1 wherein the polymer is a polyolefin.

3. A composition according to claim 1 where in the compound of component (b)
   $R_1$ is alkyl of 4 to 8 carbonatoms, $R_2$ is alkyl of 1 to 8 carbon atoms, $R_3$ and $R_4$ are each hydrogen, g is 2, T is hydrogen, alkyl of 1 to 8 cargbonatoms, phenyl, alkyl of 1 to 5 carbon atoms substituted by hydroxyl, by halogen or by —OCOG where G is alkyl of 1 to 18 carbon atoms; and E is alkylene of 2 to 10 carbon atoms.

4. A composition according to claim 1 wherein in the compound of component (b)
   $R_1$ and $R_2$ are each tert-butyl, $R_3$ and $R_4$ are each hydrogen, g is 2, T is hydrogen, phenyl, 2-hydroxyethyl or 2-bromoethyl, and E is alkylene of 4 to 8 carbon atoms.

5. A composition accoring to claim 1 wherein the compound of component (b) is 6-(3,5-di-tert-butyl-4-hydroxyphenyl)-4,5-dihydro-3(2H)-pyridazinone.

6. A composition according to claim 1 wherein the compound of component (b) is 6-(3,5-di-tert-butyl-4-hyroxyphenyl)-4,5-dihydro-2-phenyl-3(2H)-pyridazinone.

7. A composition according to claim 1 wherein the compound of component (b) is 6-(3,5-di-tert-butyl-4-hydroxyphenyl)-4,5-dihydro-2-hydroxyethyl)-3(2H)-pyridazinone.

8. A composition according to calim 1 wherein the compound of component (b) is bis-2,2'-[6-(3,5-di-tert-butyl-4-hydroxyphenyl)-4,5-dihydro-3(2H)-pyridazin-2-yl]ethyl sebacate.

9. A composition according to claim 1 wherein the compound of component (b) is bis-2,2'-[6-(3,5-di-tert-butyl-4-hydroxyphenyl)-4,5-dihydro-3(2H)-pyridazin-2-yl]ethyl adipate.

10. A composition according to claim 1 wherein the compound of component (b) is 2-(2-bromoethyl)-6(3,5-di-tert-butyl-4-hydroxyphenyl)-4,5-dihydro-3(2H)-pyridazinone.

* * * * *